United States Patent [19]

Bellmann

[11] Patent Number: 5,811,417
[45] Date of Patent: Sep. 22, 1998

[54] PROCESS FOR PRODUCING A STERILE PREDNISOLONE GEL

[75] Inventor: Günther Bellmann, Berlin, Germany

[73] Assignee: Dr. Gerhard Mann Chem.-Pharm. Fabrik GmbH, Berlin, Germany

[21] Appl. No.: 696,873

[22] PCT Filed: Jan. 17, 1995

[86] PCT No.: PCT/EP95/00155

§ 371 Date: Nov. 27, 1996

§ 102(e) Date: Nov. 27, 1996

[87] PCT Pub. No.: WO95/22333

PCT Pub. Date: Aug. 24, 1995

[30] Foreign Application Priority Data

Feb. 17, 1994 [DE] Germany ............... 4404990.0

[51] Int. Cl.⁶ ..................................... A61K 31/56
[52] U.S. Cl. ........................... 514/177; 514/178

[58] Field of Search ....................... 514/177, 178

[56] References Cited

PUBLICATIONS

Chemical Abstracts 119:234–62 (1993). Lobering et al.

*Primary Examiner*—Zohreh Fay
*Attorney, Agent, or Firm*—Chris P. Konkol

[57] ABSTRACT

The invention concerns a method for producing a sterile prednisolone gel. The method is characterized in that prednisolone or its pharmaceutically acceptable ester is sterilized and incorporated into a sterile polyacrylate gel, which has been per se conventionally produced, in appropriate amount under aseptic conditions, or else the sterile prednisolone or its pharmaceutically acceptable ester is suspended in a part of the amount of water required for producing the polyacrylate suspension and is then homogenously incorporated into the polyacryate, which is then made into a gel.

12 Claims, No Drawings

PROCESS FOR PRODUCING A STERILE PREDNISOLONE GEL

FIELD OF THE INVENTION

The invention concerns a method of producing a prednisolone gel.

BACKGROUND OF THE INVENTION

Prednisolone is a glucocorticoid, of which its anti-inflammatory effect is about two or three times stronger than other similar cortisones. Prednisolone is known as an anti-inflammatory and anti-rheumatic drug. For treating dermatological conditions and allergies, local application is preferred. As an anti-inflammatory and allergy medicine, prednisolone, to a large extent, is also used for ophthalmological purposes.

The previously used commercial preparations containing prednisolone, for topical application, particularly for the eyes, are either aqueous suspensions or ointments, since prednisolone is not sufficiently soluble in water and, therefore, must be put in suspension or in an ointment or suspension-ointment. The disadvantage of aqueous suspensions of active agents such as hormones is normally, as is known to the artisan skilled in pharmaceutical technology, the danger of so-called "caking," viz., the formation of sediment, which necessitates shaking before application of the suspension. This agitation of the medicine by the lay-person is frequently not correctly carried out and, therefore, an inaccurate dosage can occur. The disadvantage of the ointment-suspension lies in the relatively poor compatibility on account of the particle size of the prednisolone. Although compliance by the patient can significantly reduce its occurrence, eye injury on account of sedimentation can occur. There exists, therefore, a need for prednisolone in the form of a gel that has good compatibility in a preparation for topical application, especially for application to the eye. The production of such a gel, however, is very difficult, because a suspension of prednisolone or its pharmaceutically acceptable ester is not sterilizable by means of autoclaving. Heat treatment accelerates the hydrolysis of the active ingredient and, moreover, presents the danger of causing undesirable crystal growth to occur. Gels, for example of a polyacrylate gel, are actually in principle heat sterilizable, but for application to the eye, the preparation must be isotonic and isotonic agents such as sorbitol, glycerin, and the like tend to change color on heating. In other words, the ingredients in a polyacrylate gel can turn a brownish color after autoclaving, which is not acceptable to the patient.

European patent publication EP 0562 445 A2 discloses a gel with a viscosity of 10,000 to 50,0000 mpas, comprising a polyacrylate and a further polymer or polymeric mixture, for application to the eye, with customary auxiliary ingredients and optionally with one or more known ophthalmologically active ingredients.

BRIEF DESCRIPTION OF THE INVENTION

The invention concerns a method for producing a sterile prednisolone gel. The method is characterized in that prednisolone or its pharmaceutically acceptable ester is sterilized and incorporated into a sterile polyacrylate gel, which has been per se conventionally produced, in appropriate amount under aseptic conditions, or else the sterile prednisolone or its pharmaceutically acceptable ester is suspended in a part of the amount of water required for producing the polyacrylate suspension and is then homogenously incorporated into the polyacryate, which is then made into a gel.

DETAILED DESCRIPTION OF THE INVENTION

According to one embodiment of the present invention, there is now a method of producing a sterile prednisolone gel that is characterized in that a sterile polyacrylate gel is produced, but that prednisolone or its pharmaceutically acceptable salt is separately sterilized and incorporated into the acrylate gel, in a suitable amount, under aseptic conditions. Alternatively, the sterile prednisolone or its pharmaceutically acceptable ester is suspended with a part of the solution, which may contain a sterile tonicity agent, used for the production of the polyacrylate gel, and this suspension is then homogenously mixed in with the separately sterilized polyacrylate gel.

It has been shown that a sterile prednisolone gel in a polyacrylate base can be satisfactorily produced when certain method steps are followed in its production. According to one embodiment of the present invention, an aqueous polyacrylate suspension is made and then autoclaved under sterile conditions. This acrylate suspension is mixed with a sterile-filtrated solution of preserving agent, isotonicity agent, and chelating agent. After careful and thorough mixing of the starting materials, the addition of sterile-filtrated caustic soda solution initiates gel formation, and the gel is further subjected to agitation until it is homogenous. Meanwhile the prednisolone or its pharmaceutically acceptable ester is sterilized. This can be accomplished by dissolving the active substance in a suitable amount of solvent, for example ethyl acetate, subjecting the solution to sterile filtration, and precipitating the active substance, for example, through the addition of sterile water with an anti-microbial agent under aseptic conditions. The microbially sterile prednisolone or its pharmaceutically acceptable ester is then triturated or ground to a powder with about three to ten times that amount of the gel base. The remaining amount of gel is then incorporated in the concentrate by thorough mixing. The finished gel preparation is then conventionally decanted or drawn off under sterile conditions. In an alternative variation of this method, the microbially sterile prednisolone or its pharmaceutically acceptable ester can be, to a large extent, suspended in a part of the aqueous solution of the tonicity agent. The polyacrylate gel can be made in a conventional manner with the remaining amount of isotonic agent and separately the isotonic suspension of the prednisolone can be homogenously mixed with the polyacrylate under sterile conditions.

This sterile gel is well acceptable to the patient, because its application does not have the disadvantage of known ointments and is not oily. Stability has been proven, so that the gel has a relatively long shelf life without any change in its physical properties. In particular, there is no crystal growth of the active ingredient. Such a sterile gel preparation represents a significantly improved form of application in the ophthalmological field. The present invention will be further explained and illustrated by the Example that follows.

EXAMPLE

This Example illustrates a method of making a gel according to the present invention, although the production of larger amounts of gel may be necessary to meet commercial demands. In the present example, the gel is produced with water that is suitable for injection purposes (injection grade). To produce 500 g of polyacrylate gel, 1.220 g of polyacrylic acid (packaged under the trademark "Carbopol 980 NF") is carefully suspended, with the aid of an ultrasonic apparatus, in ca. 700 ml water and autoclaved for 20 minutes at 121° C. and 2 bar pressure. In 700 ml of sterile injection-grade water were then dissolved 0.050 g of benzalkonium chloride (BAK), 20.000 g sorbitol and 0.050 g of sodium EDTA (×2H2O), which was then subjected to sterile filtering (Sartorius® Cellulose nitrate filter, order no. 11307-50ACN, 0.2 µm) into a sterile vessel. The sterile-filtered salt solution was then mixed, with strong agitation, into the autoclaved polyacrylate suspension. Sterile water in the amount of 1958.121 g was then added, and the solution was subjected to further agitation for 5 to 10 minute. Subsequently, strong sodium hydroxide in the amount of 0.465 g was dissolved in exactly 40 g of injection-grade water. This caustic soda was then introduced drop-wise under agitation over a sterile filter (Millex-GS, 0.22 µm, SLGS 025 BS der Fa. Millipore). The mixture was agitated until the formation of a completely homogenous gel.

A microbially sterile prednisolone acetate in the amount of 5 g was then slowly and carefully mixed with about 30 to 50 g of the gel. The production of the prednisolone acetate followed from the dissolution of the prednisolone in ethyl acetate, sterile filtration of the solution, and separation with water containing a bacteriocide under sterile conditions. After the prednisolone is accordingly suspended in the given amount of gel, the rest of the gel, in total 495 g, is carefully incorporated into the initial material. All method steps were carried out under aseptic conditions.

The prepared gel was likewise drawn off in tubes under aseptic conditions. By an alternative method, the microbially sterile prednisolone acetate was suspended in a sterile-filtrated isotonic solution of 700 ml water, 0.050 g benzalkonium chloride, 20.000 g sorbitol and 0.050 g of disodium EDTA. This solution was then, as already described, incorporated, under strong agitation, in the autoclaved polyacrylate suspension. Further adaptation or modification of the invention, corresponding to the described production of sterile polyacrylate gel, falling within the scope of the following claims may occur to the skilled artisan.

We claim:

1. A method of producing a sterile prednisolone gel characterized in that an aqueous suspension comprising a polyacrylic acid or polyacrylate is produced and converted into a sterile polyacrylate gel, prednisolone or its pharmaceutically acceptable ester is separately sterilized and then incorporated, under aseptic conditions, into a corresponding amount of either the sterile polyacrylate gel or the aqueous suspension comprising the polyacrylic acid or polyacrylate polymer, which aqueous suspension is then transformed into a gel.

2. The method of claim 1 characterized in that the sterile polyacryate gel is produced by autoclaving an aqueous suspension comprising a polyacrylic acid or polyacrylate and adding an effective amount of a sterile caustic soda.

3. The method of claims 1 or 2 characterized in that the aqueous suspension comprising a polyacrylic acid or polyacrylateis mixed with an aqueous solution of a pharmaceutically acceptable preservative.

4. The method of claims 1 or 2 characterized in that the aqueous suspension comprising a polyacrylic acid or polyacrylate is mixed with a sterile solution of a complexing agent.

5. The method according to claims 1 or 2 characterized in that the aqueous suspension of a polyacrylic acid or polyacrylate is mixed with a sterile aqueous solution of an isotonicity agent.

6. The method according to claims 1 or 2 characterized in that the prednisolone or its pharmaceutically acceptable ester is dissolved in a solvent for prednisolone, subjected to sterile filtration, separated out, and microbially sterilized under sterile conditions.

7. The method according to claims 1 or 2 characterized in that the desired total amount of prednisolone or its pharmaceutically acceptable ester is triturated, under aseptic conditions, with about 1/10 of the total amount of polyacrylate and then incorporated in a homogenous mixture with the rest of the gel.

8. A method according to claims 1 or 2 for the production of a sterile prednisolone gel characterized in that the sterile prednisolone or its pharmaceutically acceptable ester is suspended with a sterile solution of a tonicity agent, preservative, and complexing agent, and then mixed with a sterile suspension of the polyacrylic acid or polyacrylate, which is then converted into a gel.

9. A method according to claim 3 characterized in that the aqueous suspension comprising a polyacrylic acid or polyacrylate is mixed with an aqueous solution of benzalkonium chloride.

10. The method of claim 4 characterized in that the aqueous suspension comprising a polyacrylic acid or polyacrylate is mixed with a sterile solution of EDTA or its pharmaceutically acceptable salt.

11. The method according to claim 5 characterized in that the aqueous suspension of a polyacrylic acid or polyacrylate polymer is mixed with a sterile aqueous solution of sorbitol.

12. A method of producing sterile prednisolone gel characterized in that an aqueous suspension comprising a polyacrylate acid or polyacrylate is produced and converted into a sterile polyacrylate gel, prednisolone or its pharmaceutically acceptable ester is separately sterilized and then incorporated, under aseptic conditions, into a corresponding amount of either the sterile polyacrylate gel or the aqueous suspension comprising the polyacrylic acid or polyacrylate polymer, which aqueous suspension is then transformed into a gel, wherein the sterile polyacrylate gel is produced by autoclaving and the prednisolone or its pharmaceutical acceptable ester is dissolved in a solvent for prednisolone and subjected to sterile filtration prior to being incorporated into the sterile polyacrylate gel or into the aqueous suspension comprising the polyacrylate acid or polyacrylate polymer that is subsequently transformed into a gel.

* * * * *